United States Patent
Ghosal

(10) Patent No.: US 6,558,712 B1
(45) Date of Patent: May 6, 2003

(54) DELIVERY SYSTEM FOR PHARMACEUTICAL, NUTRITIONAL AND COSMETIC INGREDIENTS

(75) Inventor: Shibnath Ghosal, Benares (IN)

(73) Assignees: Natreon Inc., New Brunswick, NJ (US); Indian Herbs Research & Supply Company Ltd., Saharanpur (IN)

( * ) Notice: Subject to any disclaimer, the term of this patent is extended or adjusted under 35 U.S.C. 154(b) by 0 days.

(21) Appl. No.: 09/957,797

(22) Filed: Sep. 21, 2001

(51) Int. Cl.$^7$ ............................................. A61K 35/78
(52) U.S. Cl. ........................ 424/725; 424/400; 424/401; 424/195.18; 424/484
(58) Field of Search ........................... 424/195.18, 725, 424/401, 408, 452, 465, 488, 400, 484

(56) References Cited

PUBLICATIONS

Ghosal, S., Indian J. Indg. Med. (1992), 9, (1&2) "Shilajit: Its Origin and Significance". A general bioactivity–directed investigation of shilajit collected from rocks. No defined purified shilajit composition is disclosed.

Rowland, D. U.S. Pat. 5,405,613, issued Apr. 11, 1995 "Vitamin/Mineral Composition". An undisclosed composition of iron shilajit in a multi–vitamin and/or mineral preparation is described.

Ghosal, S. et al, Phytotherapy Research 9, 000–000 (1995) "Shilajit Induced Morphometric and Functional Changes in Mouse Peritoneal Macrophages". Collected shilajit from rocks and tested for its effect on mouse peritoneal cells.

Bhattacharya, S. et al, Phytotherapy Research 7, 1 (1993), "Effects of Shilajit on Biogenic Free Radicals". The organic exudation of humic substances on rocks was processed by the Ghosal method of 1993b (see below) and its effect on free radicals was determined.

Alam, M. et al, B.M.E.B.R.vol. IV, No. 1–2, pp. 54–61 "Studies on Authentic Silajat Samples". Analysis of crude shilajit.

Kong, Y. et al., Int. J. Crude Drug Res. 25 (1987) No. 3, pp. 179–182. "Chemical Studies on a Nepalese Panacea–Shilajit (I)". Describes analysis of an alcohol extract of shilajit, and of the residue therefrom; analysis of the water–insoluble part and recrystallization of the aqueous extract. No purified shialjit composition is described.

Ghosal, S., J. Indian Chem. Soc., vol. 71 (1994) "Shialjit Odour: Its Origin and Chemical Character". The volatile constituents of crude shilajit were identified as being the compounds responsible for its odor.

Ghosal, S. et al. Phytotherapy Research, vol. 5, 211–216 (1991). "The Need for Formulation of Shilajit by its Isolated Active Constituents". Crude shilajit was collected and purified to provide an undisclosed mixture of unidentified low $M_w$ organic compounds and (fulvic acids).

Ghosal, S. "Traditional Medicine" Proceedings of an International Seminar Nov. 7–9 (1992). Oxford Publishing Co. (India) pp. 308–319. "Shilajit : Its Origin and Vital Significance". A review paper on the chemistry of the core cosntituents of humus and the similarity of its compounds to those found in crude shilajit.

Ghosal et al, J. Pharmaceutical Sciences 65, No. 5 "Shilajit I : Chemical Constituents". Extraction of crude shilajit with solvents of graded polarity gave three different classes of organic compounds. No resultant purified shilajit compositions was disclosed.

Ghosal et al. Phytotherapy Research 2, No. 4 (1988) pp. 187–191. "Anti–Ulcerogenic Activity of Fulvic Acids and 4'–Methoxy–6–carbomethoxybiphenyl Isolated from Shilajit". Crude shilajit was extracted successively with hot organic solvents to remove free low Mr organic compounds (MCB). An aqueous solution of the remaining material was acidified and fulvic acids (FAs) were collected from the supernatant liquid. Each of these compounds were tested separately and together for their effect on gastric ulcers induced by stress and aspirin. No purified shilajit compositions with a defined ratio of bio–active constituents were described.

Ghosal, S. Pure and Appl. Chem. 62, No. 7 (1990) 1285–8 "Chemistry of Shilajit, an Immunomodulatory Ayurvedic rasayan". A review paper on the humic acid and fulvic acid constituents of shilajit and their chemical formulas.

Ghosal, S. Soil Biol. Biochem 23, No. 7, (1991) pp. 673–680. "The Core Structure of Shilajit Humus". An extract procedure wa described for isolation of shilajit–humic acids (HAs), fulvic acids (FAs) and freshly–released low molecular–weight organic compounds. Other solvent treatments enabled identification of several individual components of crude shilajit. No purified shilajit compositions were described.

Ghosal, S. et al. Phytotherapy Research vol. 7, 29–34 (1993). "Effects of Shilajit and its Active Constituents on Learning and Memory in Rats". Crude shilajit was extracted to provide several test compounds for evaluation of their effect on learning and memory.

(List continued on next page.)

Primary Examiner—Leon B. Lankford, Jr.
Assistant Examiner—Ruth A. Davis
(74) Attorney, Agent, or Firm—Walter Katz

(57) ABSTRACT

A stable, water-soluble delivery system of a purified Shilajit composition obtained by extraction of native Shilajit, containing at least 40% by weight of a carrier which is purified fulvic acid, characterized by having a sponge-like structure punctured by voids of about 200–1000 Å in diameter, and a Mn molecular weight of about 700–2500; and an effective amount of an active pharmaceutical, nutritional or cosmetic ingredient added to said carrier and filling voids therein.

8 Claims, No Drawings

OTHER PUBLICATIONS

Ghosal, S. et al. Soil Biol. Biochem 25, No. 3 (1993) p. 377–81. "Similarities in the Core Structures of Shilajit and Soil Humus". Extracted humus from crude shilajit left after removal of loosely–bound low Mw organic compounds was fractionated into fulvic acids, humic acid and humins. The low Mw organic compounds were separated into individual components. No purified shilajit composition was disclosed.

Ghosal, S. et al. Indian J. of Chem. 34B, Jul. 1995, p 591–5. "Free Radicals of Shilajit Humus". Reaction of individual components of shilajit with free radicals.

Ghosal, S. et al. Indian J. of Chem. 34B, Jul. 1995, p 596–602. "Interaction of Shilajit with Biogenic Free Radicals". Described a general extraction procedure for making processed shilajit, without, however, disclosing the chemical constituents of the processed shilajit.

Ghosal, S. et al. J. Chem. Res. (1989) 350–351. "Shilajit Part 4. Chemistry of Two Bioactive Benzopyrone Metabolites". The structures of fulvic acid and oxygenated dibenzo–α–pyrones were confirmed by chemical synthesis.

DELIVERY SYSTEM FOR PHARMACEUTICAL, NUTRITIONAL AND COSMETIC INGREDIENTS

CROSS-REFERENCE TO RELATED U.S. PATENT APPLICATION

This application is related to co-pending application Ser. No. 09/860,890, filed May 18, 2001, by the same inventor as herein, and assigned to the same assignee.

BACKGROUND OF THE INVENTION

1. Field of the Invention

This invention relates to delivery systems for active ingredients, and, more particularly, to a water-soluble delivery system for pharmaceutical, nutritional and cosmetic active ingredients, which includes a purified Shilajit composition obtained by extraction from native Shilajit containing a carrier which is purified fulvic acid, and, wherein the active ingredient is added to and present in voids of the carrier.

2. Description of the Prior Art

Native Shilajit is a blackish-brown exudation, of variable consistencies, obtained from steep rocks of different formations found in the Himalayas at altitudes between 1000–5000 m, from Arunachal Pradesh in the East, to Kashmir in the West. Shilajit also is found in other mountain ranges of the world, e.g. Afganisthan (Hindukush, Badakh-Shan), Australia (Northern Pollock Ranges), and in the former USSR (Tien-Shan, Pamir, Caucasus, Ural). Native Shilajit is believed to arrest aging and also produce rejuvenation, two important attributes of an Ayurvedic rasayan medicine. Considerable controversy, however, has existed in the literature concerning the nature and chemical character of Shilajit. It has been variously described as a bitumen (asphalt), a mineral resin, a plant fossil, a substance of mixed plant and animal origin, or an inorganic substance.

Generally, native Shilajit contains two classes of organic compounds, namely, (a) humic substances and (b) non-humic organic metabolites. Humic substances are the the major organic constituents of native Shilajit, present in an amount of about 80–85% therein; these substances have molecular weights ranging from several thousand for humic acids (HAs), to up to several million for polymeric humins (HMs) and only a few hundred for its fulvic acid (FAs) component. Humic substances also are found in soils and sediments distributed over the earth's surface, occurring in almost all terrestrial and aquatic environments. Sedimentary rock humic substances are produced by the interactions of marine fossils, plants, algae and mosses (bryophtes) with microorganisms, by a process known as humification. Humification of latex-and resin-bearing plants is primarily responsible for the production of water-soluble humic substances.

The non-humic substances of Shilajit are low molecular weight ($M_w$) compounds of marine fossil, plant and microbial origin, occurring in and around Shilajit-bearing rocks. The remaining non-humic organic masses in Shilajit comprise a mixture of low $M_w$ aromatic, aliphatic alicyclic, and heterocyclic (N- and S-containing) compounds. Of particular biological interest are low $M_w$ oxygenated dibenzo-α-pyrones (DBP) and hydroxyacetophenones (HAPs).

The ancestral origin of Shilajit now has been established as invertebrate fossils of the phylum: Mollusca, of the Mesozoic period (60–200 million years ago). Shilajit arises from the continental drift and plate tectonic effect, reached from the ocean-bed to sedimentary mountain top; and by bacterial interaction-humification which formed Shilajit humus-paleohumus. However, native Shilajit material varies considerably with respect to quality and the amount of bioactive materials therein. Furthermore processing of native Shilajit involves very complicated and tedious procedures. Recently, collection of good quality native Shilajit material has been improved so that, correspondingly, the output of a purified Shilajit product can be expected to be much improved.

The biological effects of Shilajit are believed to be due to the two distinct classes of bioactive compounds, namely: (i) DBPs, both mono- and bis-compounds thereof, in free and metal-ion conjugated forms; and (ii) fulvic acids (FAs) from Shilajit-humic substances, which function as a carrier for the bioactive DBPs. However, native Shilajit rhizospheres from different origins suffer from the presence of only small amounts of such bioactive compounds. Large amounts of contaminants, e.g. high $M_w$ polymeric quinones, humins (HMs), and inorganic substances; however, are present. Shilajit rhizospheres also are heavily infested at its periphery with a large array of microorganisms, some of which are producers of mycotoxins. Thus, the potential risk of ingesting Shilajit in its native form, or only after rudimentary purification, with no control or defined standards, is quite apparent.

The prior art in this field is described in the "Information Disclosure Statement", attached hereto; these references are located in the related co-pending patent application. Other cumulative prior art is exemplified by the following references:

(1) S. Ghosal et al, Phytotherapy Res., 1991, 5, 211.
(2) S. Bhaumik, S. Chartopadhyay and S. Ghosal, Phytotherapy Res., 1993, 7, 425.
(3) Y. C. Kong et al, Int. J. Crude Drug Res., 1987, 25, 179.
(4) S. Ghosal, S. K. Singh and R. S. Srivastava, J. Chem. Res., 1988, 196.
(5) M. V. S. Sultanbawa, Tetrahedron, 1980, 36, 1465.
(6) S. B. Scharya et al, Indian J. Exp. Biol., 1988, 26, 775.
(7) S. Ghosal et al, Phytotherapy Res., 1989, 6, 249.

Accordingly, it is an object of this invention to provide a purified water-soluble delivery system for active ingredients such as pharmaceutical, nutritional and cosmetic ingredients using a purified fulvic acid carrier having voids therein into which an active ingredient can be incorporated for effective and controlled delivery of the active therefrom.

Another object of this invention is to provide such a delivery system which can augment the bioavailability of drugs for the user.

A feature of the invention is the provision of a stable delivery system including a purified fulvic acid carrier having predetermined molecular weight and void sizes which can accept different active ingredients advantageously to deliver and release them smoothly at cell-receptor sites.

Another feature of the invention is the enhanced water solubility of active drug ingredients.

These and other objects and features of the invention will be made apparent from the following description thereof.

SUMMARY OF THE INVENTION

What is provided in this invention is a stable, water-soluble delivery system which includes (a) a purified Shilajit composition preferably containing at least 40% by weight of purified fulvic acid carrier, obtained by extraction of native Shilajit so that the fulvic acid carrier is substantially without bioactive components therein. The purified fulvic acid carrier is characterized by having a sponge-like structure punctured by voids of about 200–1000 Å in diameter and a molecular weight, $\overline{M}n$, of about 700–2500, ($\overline{M}n$ is a number average molecular weight); and (b) an active material, e.g. a water-insoluble ingredient, added to and filling voids in the purified fulvic acid carrier.

Preferably, the purified fulvic acid carrier has an $E_4/E_6$ absorption ratio of about 6–10, at λ 465/665 nm.

Most preferably, the delivery system of the invention potentiates the bioactivity of a drug, nutritional or cosmetic ingredient incorporated into the voids of the purified fulvic acid carrier.

Still most preferably, the active ingredient suitably is present in an amount of about 0.5 to 40% by weight of the fulvic acid carrier.

DETAILED DESCRIPTION OF THE INVENTION

The difference between Shilajit-based fulvic acid (FAs) and alluvial soil-derived fulvic acids lies in the core structures of the fulvic acids (FAs) in these compositions. Shilajit-FAs contains 3,8-oxygenated dibenzo-α-pyrone as the core nucleus, which, upon repeated oxidation, and Michael addition reactions by nucleophile-containing oxygen, nitrogen and carbon ions, in association with various lipid moieties, produce a multiplayer micellar structure. In contrast, alluvial soil-FAs are composed essentially of aromatic hydroxy acids and polyphenols derived from phenolic oxidations. Both these FAs contain different metal ions, especially Fe, Co, Zn, Ca, etc., associated with the FAs. The metals in Shilajit-FAs are well-organized, multicentered, metal-ion associated products which, in the case of iron, maintains the metal in the reduced state and produce different iron-containing enzymes. Such trace ion-metal associations are not possible for soil-FAs because they have a much less organized heteropolycondensate structure whose micellar structure is irregular.

Another unique feature of Shilajit-FAs is that it is of endogenous origin produced by animal systems. These systems meet the essential need of bioavailability of trace metals and minerals, which serve as a carrier of essential nutrients in the living animal body. By contrast, soil-FAs, being exogenous in origin, do not contribute to those essential needs of animals.

Shilajit-FAs also contains oligomeric (di, tri, tetra) dibenzo-α-pyrones, which scavenge free radicals and free metal ions, to become a soft-spin radical. In contrast, soil-FAs contain only esters of phenolic acids which do not have the antioxidant activity possessed by Shilajit-FAs.

Significantly, acylated DBP, with a lipid chain, are present in Shilajit-FAs; these actives behave like a liposome (polymicellar structure) which can act as an efficient carrier molecule. The phenolic acid esters present in soil-FAs do not possess these characteristics.

Thus, in accordance with the invention, the purified fulvic acid carrier constituent of native Shilajit, without toxic components, and substantially without bioactive constituents in the voids of the carrier, is provided by a defined extraction procedure from native Shilajit.

The purified Shilajit composition containing the purified fulvic acid carrier is obtained by an extraction procedure from native Shilajit rock exdudate, according to the following steps:

(a) powdering native Shilajit exdudate and dissolving it in water as solvent, (b) filtering the mixture to remove insoluble substances, (c) evaporating water from the filtrate to obtain a brown viscous residue, (d) extracting the residue with a hot organic solvent, e.g. methanol, to obtain both a soluble fraction and an insoluble Shilajit-humic fraction, (e) adding dilute aqueous NaOH to the insoluble Shilajit-humic fraction to precipitate polymeric quinones, (f) acidifying the alkaline filtrate to a pH below about 3 to precipitate humic acids, leaving a brown acidic solution of fulvic acids, (g) fractionating the acidic solution by passing it over activated carbon to provide a solution of low-to-medium $M_w$ fulvic acids, (h) passing the fulvic acid solution through a $H^+$ ion-exchange resin to concentrate the fulvic acids in solution, and (i) evaporating the solution.

The thus-obtained extraction product is a purified Shilajit composition preferable containing at least 40% by weight of purified fulvic acid carrier, and it is substantially without bioactive components therein. The fulvic acid has a sponge-like structure punctuated by voids of about 200–1000 Å in diameter and an $\overline{M}n$ of about 700–2500. The active material then is added to the carrier to fill voids in its structure, thus-forming the desired delivery system. Upon dissolution in water, the active ingredient is released to perform its intended active function, e.g. a pharmaceutical, nutritional or cosmetic function.

A. The Active Ingredient (Pharmaceutical, Nutritional and Cosmetic Ingredients)

Any ingredient used to treat or affect the body, both topical and systemic, can be incorporated as the active agent into the polymeric carrier of this invention. An active ingredient thus includes drugs, nutrients, cosmetics, cosmeceuticals, diagnostic agents, or a salt, isomer or derivative thereof, and mixtures thereof.

As used herein, the term "drug" or any other similar term, means any chemical or biological material or compound suitable for administration by the methods previously known in the art and/or by the methods taught in the present invention that induces a desired biological or pharmacological effect, which may include but is not limited to (1) having a prophylactic effect on the organism and preventing an undesired biological effect such as preventing an infection, (2) alleviating a condition caused by a disease, for example, alleviating pain or inflammation caused as a result of disease, (3) either alleviating, reducing, or completely eliminating a disease including actinic aging of the organism and/or (4) protecting skin from photodamage. The effect may be local, such as providing for a local anesthetic effect, or it may be systemic. This invention is not drawn to novel drugs or to new classes of bioactive agents. Rather it is limited to the compositions and methods of delivery of agents that exist in the state of the art or that may later be established as active agents and that are suitable for delivery by the present invention. Such substances include broad classes of compounds normally delivered into the body by systemic or topical route. In general, this includes but is not limited to: anti-infectives such as antibiotics and antiviral agents; analgesics and analgesic combinations; anorexics; anthelmintics; antiarthritis; antiasthamatic agents; anticonvulsants; anticancer, antidepressants; antidiabetic agents; antidiarrheals; antihistamines; anti-inflammatory agents; antimigraine preparations; antinauseatics; antineoplastics; anti-Parkinson drugs; antipruritics; antipsychotics; anti-cancer agents; antipyretics; antispasmodics; anticholinergics; sympathomimetics; xanthine derivatives; carodiovascular preparations including potassium and calcium channel blockers, beta-blockers, alpha-blockers, and antiarrhythmics; antihypertensives; diuretics and antidiuretics; vasodilators including general coronary, peripheral and cerebral; central nervous system stimulants; vasoconstrictors; cough and cold preparations, including decongestants; hormones such as estradiol and other steroids, including corticosteroids; hypnotics; immunosuppressives; muscle relaxants; parasympatholytics; psychostimulants; sedatives; tranquilizers; sunscreens; anti-aging ingredients. By the method of the present invention, both ionized and nonionized pharmaceutical, nutritional or cosmetic actives may be delivered, as can they be either high or low molecular weight. Also included in the scope of these terms are nucleic acids, such as DNA, RNA, and oligonucleotides.

As used herein, "effective amount" means an amount of a drug or bioactive or agent that is non-toxic but sufficient to provide the desired local or systemic effect and performance at a reasonable benefit/risk ratio attending any pharmaceutical, nutritional or cosmetic treatment.

As used herein, "peptide" means peptides of any length and includes proteins. The terms "polypeptide" and "oligopeptide" are used herein without any particular intended size limitation, unless a particular size is otherwise stated. Typical of peptides that can be utilized are those selected from the group consisting of oxytocin, vasopressin, adrenocorticotropic hormone, epidermal growth factor, prolactin, or luteinising hormone releasing hormone, growth hormone, growth hormone releasing factor, insulin, somatostatin, glucagons, interferon, gastrin, tetragastrin, pentagastrin, urogastroine, secretin, calcitonin, enkepalins, endorphins, angiotensins, rennin, bradykinin, bacitracins, polymixins, colistins, tyrocidin, gramicidines, and synthetic analogues, modifications and pharmacologically active fragments thereof, monoclonal antibodies and soluble vaccines. The only limitation to the peptide or protein drug, which may be utilized, is one of functionality.

As used herein, a "derivative" of a carbohydrate includes, for example, an acid form of a sugar, e.g. glucuronic acid; an amine of a sugar, e.g. galactosamine; a phosphate of a sugar, e.g. mannose-6-phosphate; and the like.

As used herein, "administering" and similar terms mean delivering the composition to the individual being treated such that the composition is capable of being circulated systemically to the parts of the body where the composition binds to targeted cells and is taken up by endocytosis. Thus, oral subcutaneous, intramuscular, or intravenous administration, or intraperitoneal administration preferably administers the composition to the individual by topical or systemic administration. Injectables for such use can be prepared in conventional forms, either as a liquid solution or suspension or in a solid form suitable for preparation as a solution or suspension in a liquid prior to injection, or as an emulsion. Suitable excipients include, for example, water, saline, dextrose, glycerol, ethanol, and the like; and if desired, minor amounts of auxiliary substances such as wetting or emulsifying agents, buffers, and the like can be added.

B. The Carrier

The fulvic acid carrier in this invention is based on naturally occurring, toxicologically safe metabolites (e.g. 3,8-dihydroxy-dibenz-α-pyrone, DBP, 4' methoxy-6-carbomethoxybiphenyls, MCB). The purified fulvic acids (FAs) in this invention are polymeric units of 3,8-oxygenated dibenz-α-pyrone repeat units having the general formula:

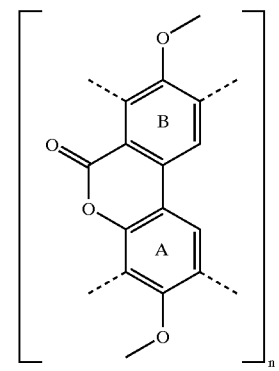

A suggested sequence for the formation of fulvic acid in nature is given below:

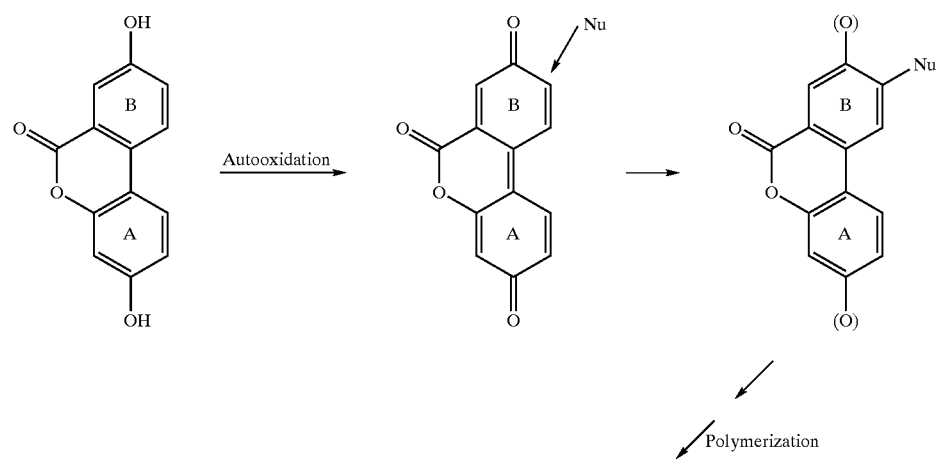

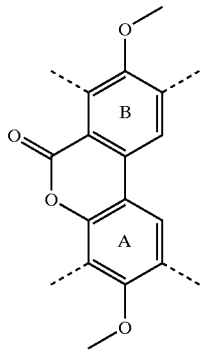

where: Nu=a nucleophile, e.g . RO, RNH⁻, $RCO_2^-$ etc.

In this invention, generally higher mol. wt. (e.g. $\overline{M}n$ 2000) purified fulvic acid carriers are used for delivering high molecular wt. drugs, e.g. polypeptides, etc., which otherwise would not cross the membrane barrier. Low mol. wt. fulvic acid (e.g. $\overline{M}n$<1000, voids 200–500 Å) is preferred for delivering purified low molecular weight drugs.

In the delivery system of the invention, the active ingredient is physically and/or chemically bound within the voids of the fulvic acid carrier by hydrophobic bonding, ligand-complex/chelation, reversible covalent bonding and/or charge-transfer complexes.

The active ingredient is incorporated into its fulvic acid carrier by simple blending, e.g. by stirring in a common solvent, or by dry-powder admixture, with or without an added third component.

The invention especially provides a delivery system composition of pharmaceutical, nutritional or cosmetic compounds for oral or topical administration, particularly a water-insoluble ingredient, using a purified Shilajit composition containing at least 40% by weight of purified fulvic acid as defined hereinbefore.

The invention also provides a method of administration of such composition to a subject, which comprises administering it orally, topically or parentally.

The formulations according to the invention may be used for known indications of the particular pharmaceutical, nutritional or cosmetic compound incorporated therein.

The effective amounts of pharmaceutical, nutritional or cosmetic compound and of the formulation to be administered depends on a number of factors, e.g. the condition to be treated, the desired duration of treatment, and the rate of release of the compound.

The desired formulations may be produced in a known manner. The amount of the pharmaceutical, nutritional or cosmetic active agent required and the release rate thereof may be determined on the basis of known in vitro or in vivo techniques, e.g. how long a particular active agent concentration in the blood plasma or on skin remains at an acceptable level. The degradability of the matrix may also be obtained by in vitro or especially in vivo techniques, for example wherein the amount of matrix materials in the subcutaneous tissue is determined after particular time periods.

Suitably the active ingredient is present in an effective amount, preferably about 0.5 to 40% by weight of the purified fulvic acid carrier.

The invention will be described hereinafter with reference to the following examples.

Example 1

Purified Fulvic Acid-Glibenclamide Drug Delivery System

Glibenclamide (Gb) is an oral hypoglycaemic agent of the sulfonyl urea group; however it is only sparingly soluble in water. Gb (1 mg) is only 10–12% soluble in 1.0 ml water at room temperature, as determined by HPTLC (Gb, λ max 232 nm). However, purified fulvic acid-Gb compositions (1:10, wt/wt, 1.0 mg) are completely soluble in water (0.1 ml), and the solution remains stable for over a week. The identity of Gb is concealed therein by the micellar cover of the fulvic acid (HPTLC). The composition also exhibits an increased hypoglycaemic action. Specifically, albino rats, made partially diabetic by administering streptozotocin (Stz, 40 mg/kg, orally, p.o.), were administered with both a Gb (1.0 mg/kg, water-suspension, p.o.) and a Gb-fulvic acid composition (1:10, 10 mg/kg, p.o.), separately (n=10). Gb itself did not exhibit any noticeable blood sugar lowering effect. In contrast, the Gb-fulvic acid composition lowered the plasma glucose level (PGL) by 20–24% over the control value. This effect was maintained for 3 hours. Fulvic acid itself (0.1 mg/kg, s.c. or 10 mg/kg, p.o.) only marginally lowers the PGL in albino rats.

Example 2

Potentiation of Anti-Diabetic Effect of Insulin (p.o.) by Purified Fulvic Acid-Insulin Compositions Streptozocin (Stz)-induced diabetic (SID) rats were used for this study. Insulin (I, 1.0 U/kg, p.o.) produed only marginal lowering (<10%) of plasma glucose level (PGL) in SID rats. Smaller doses (I, 0.25 and 0.5 U/kg p.o.) did not exhibit any PGL lowering effect. By contrast, purified fulvic acid-insulin compositions (0.25 U/kg+10 mg/kg, p.o.) produced a 25% lowering, and Fulvic Acid-Insulin compositions (0.5 U/kg+10 mg/kg, p.o.) produced a 38% lowering of PGL in SID rates. The effect lasted for 6 hours.

Example 3

Pentazocin (Ptz)-Purified Fulvic Acid Carrier Compositions

Ptz is a narcotic opioid analgetic which shows an extensive first pass effect when given orally. The bioavailability of Ptz administered orally is only 30–35%. The first pass effect varies from species to species. In rats, up to 240 mg/kg, p.o. of Ptz does not exhibit any analgetic effect. A 1:5 (wt/wt) of Ptz-purified fulvic acid composition (80 mg/kg, p.o.), however, produced a marked analgetic effect in albino rats. The peak effect appeared within 30 min and lasted for 120 min. In human volunteers, oral doses of 50 mg of Ptz was found to be an effective analgetic equivalent to 60 mg of codeine measured by the time of onset (60 min) and duration (120 min) of analgesia. Ptz-Fulvic acid (5 mg+50 mg) compositions, given orally, produced a marked analgetic effect which appeared within 30 min and lasted for 180 min. The identity of Ptz (HPTLC), λ max 278 nm) was masked in the composition by the micellar cover of Fulvic Acid.

Use Formulations of Invention System

A. Personal Care/Cosmetics

Example 4

SKIN REJUVENATING (O/W) LOTION

| Ingredients | % (w/w) |
|---|---|
| Phase A | |
| Polyglyceryl-3 Methyl Glucose Distearate | 3.50 |
| Glyceryl Stearate, PEG-100 Stearate | 2.50 |
| Dicapryl ether | 5.00 |
| Coco-Caprylate/Caprate | 5.00 |
| Propylene Glycol Dicaprylate/Dicaprate | 3.00 |
| Almond Oil | 2.00 |
| Cetyl alcohol | 1.50 |
| Purified Shilajit/Fulvic Acid Composition (containing 0.1% retinoic acid) | 2.00 |
| Phase B | |
| Glycerin | 3.00 |
| Propylene glycol | 3.00 |
| Allantoin | 0.20 |
| Methylparaben | 0.15 |
| Water, deionized | q.s. |
| Phase C | |
| Phenoxyethanol and Isopropylparaben and Isobutylparaben and Butylparaben | 0.50 |
| | 100.00 |

Procedure

Combine A, stir and heat to 65° C. Combine B, stir and heat to 65° C. Add A to B while stirring. Homogenize at moderate speeds to avoid foaming, while allowing mixture temperature to cool to 40° C. Add C, homogenize. Stir gently until mixture is homogeneous.

Example 5 below illustrates the effectiveness of the composition of the invention in enhancing the activity of sunscreen formulations.

Example 5

SUNSCREEN O/W LOTION (SPF 20)

| Ingredients | % (w/w) |
|---|---|
| Phase A-1 | |
| Propylene Glycol Isoceteth-3 Acetate | 5.00 |
| Octyl methoxycinnamate | 7.50 |
| Benzophenone-3 | 3.00 |
| Homomenthyl Salicylate | 7.00 |
| Steareth-2 | 0.40 |
| Steareth-10 | 0.80 |
| Acrylates/$C_{10-30}$ Alkyl Acrylate Crosspolymer | 0.18 |
| Synthetic Wax | 0.80 |
| Dimethicone | 1.00 |
| Purified Shilajit/Fulvic Acid Composition | 5.00 |
| Phase B | |
| Demineralized water | 50.0 qs |
| Phase C | |
| Demineralized water | 19.82 |
| Phenylbenzimdazole sulfonic acid | 1.00 |
| Propylene glycol | 2.00 |
| Triethanolamine | 0.90 |
| Propylene Glycol and DMDM Hydantoin and Methylparaben | 1.00 |
| | 100.00 |

Procedure

Combine A, stir and heat to 80° C. Heat B to 80° C. Add A to B while stirring with a propeller mixer. Continue stirring A/B for 20 minutes while maintaining the temperature between 70–75° C. Combine C, heat and stir to 45° C. until dissolved. Add C to A/B with agitation. Qs water. Gently homogenize A/B/C allowing mixture to cool to room temperature. Adjust pH to 7.1–7.3 with TEA. Use high shear spray device to dispense.

B. Pharmaceutical and Nutritional Supplements

Example 6

PURIFIED FULVIC ACID-GLIBENCLAMIDE TABLETS AND CAPSULES

| Ingredient | (w/w, in %) | Quantity per tablet (mg) |
|---|---|---|
| 1. Purified Fulvic Acid - Glibenclamide Composition | 60.0 | 250.0 |
| 2. Avicel pH 101 | 20.0 | 84.0 |
| 3. Starch 1500 | 17.5 | 75.5 |
| 4. Stearic acid, N.F. (powder) | 2.0 | 8.5 |
| 5. Cab-O-Sil | 0.5 | 2.0 |

Note. The purified fulvic acid composition is granulated with starch paste to make it a free-flowing powder. Blend all the ingredients, except 4, for 25 min. in a blender. Screen in 4 and blend for an additional 5 min. Compress into tablets using 7/16-in standard concave tooling. Alternately, the blended material can be filled into appropriate capsules.

Example 7

"MAINTENANCE" MULTIVITAMIN TABLETS

| Ingredient | (w/w, in %) | Quantity per tablet (mg) |
|---|---|---|
| 1. Vitamin A acetate (dry form 500 IU and 500 $D_2$ per mg) | 5.5 | 11.0 |
| 2. Thiamine mononitrate, USP | 0.8 | 1.65 |
| 3. Riboflavin, USP | 1.1 | 2.10 |
| 4. Pyridoxine HCl, USP | 1.0 | 2.10 |
| 5. 1% Cyanocobalamine (in gelatin) | | |
| 6. D-Calcium pantothenate, USP | 3.75 | 7.50 |
| 7. Purified Shilajit/Fulvic acid Composition | 33.25 | 66.50 |

"MAINTENANCE" MULTIVITAMIN TABLETS -continued

| Ingredient | (w/w, in %) | Quantity per tablet (mg) |
|---|---|---|
| (containing Vitamin C) | | |
| 8. Niacinamide | 11.0 | 22.00 |
| 9. DiTab | 13.1 | 26.20 |
| 10. Microcrystalline cellulose, N.F. | 25.0 | 50.00 |
| 11. Talc, USP | 3.0 | 6.00 |
| 12. Stearic acid, (powder), N.F. | 1.5 | 3.00 |
| 13. Magnesium stearate, (powder), N.F. | 1.0 | 2.00 |

Blend all ingredients for 20 min in a suitable blender. Screen in 12 and blend for an additional 5 min. Compress at a tablet weight of 200 mg using ⅜-in standard concave tooling. Alternately, blended material is filled into a capsule containing 200 mg of multi-vitamins. These tablets or capsules can be used as nutritional supplements.

Example 8

Vitamin B-Complex Capsules

| ITEM # | INGREDIENT | MG/CAPSULE |
|---|---|---|
| 1 | Vitamin B-1, Thiamine HCl | 50.00 |
| 2 | Vitamin B-2, Riboflavin | 50.00 |
| 3 | Niacinamide | 50.00 |
| 4 | Vitamin B-6, Pyridoxine HCl | 50.00 |
| 5 | Folic Acid 10% Trituration | 4.00 |
| 6 | Vitamin B-12, Cyanocobalamin 1% Trituration | 5.00 |
| 7 | Biotin 1% Trituration | 5.00 |
| 8 | Calcium Pantothenate | 50.00 |
| 9 | PABA | 50.00 |
| 10 | Purified Shilajit/Fulvic Acid Composition | 0.40–4.00 |
| 11 | Choline Bitartrate | 50.00 |
| 12 | Inositol | 50.00 |
| 13 | Microcrystalline Cellulose | q.s. |
| 14 | Silicon Dioxide | 10.00 |
| 15 | Magnesium Stearate | 6.00 |
| 16 | Capsule #0 | 95.00 |
| | TOTAL | 575.00 |

Method of Preparation
1. Pass items 1–14 through a 30 mesh screen and blend in a V-Blender or a Double Cone Blender for 20 minutes.
2. Now add, item # 15 to the blender and blend for an additional 5 minutes.
3. Fill into Size 0 capsules with a target weight of 575 mg/capsule.

Example 9

Multi-Mineral Tablets

| ITEM # | INGREDIENT | MG/TABLET |
|---|---|---|
| 1 | Calcium Citrate | 125.00 |
| 2 | Calcium Hydroxyapatite | 62.50 |
| 3 | Calcium Carbonate | 62.50 |
| 4 | Magnesium Oxide | 93.75 |
| 5 | Magnesium Citrate | 93.75 |
| 6 | Zinc Monomethionine | 3.75 |
| 7 | Selenomethionine | 0.025 |
| 8 | Copper Aspartate | 0.25 |
| 9 | Manganese Arginate Complex 20% | 2.50 |
| 10 | Chromium Polynicotinate | 0.025 |
| 11 | Molybdenum AAC 0.2% | 0.013 |
| 12 | Potassium Citrate | 25.00 |
| 13 | Vitamin D3 Cholecalciferol 100 M iu/g | 25.00 |
| 14 | Kelp 0.5% Iodine | 0.057 |
| 15 | Vanadium AAC 0.2% | 0.007 |
| 16 | Boron Citrate/Aspartate/Glycinate 5% | 0.25 |
| 17 | Betaine HCl | 40.00 |
| 18 | Bentonite Clat Trace minerals | 5.00 |
| 19 | Purified Shilajit/Fulvic Acid Composition | 4.00–40.00 |
| 20 | Cellulose Powder | q.s. |
| 21 | Croscarmellose Sodium | 50.00 |
| 22 | Silicon Dioxide | 20.00 |
| 23 | Magnesium Stearate | 10.00 |
| 24 | Pharmaceutical Glaze | 20.00 |
| | TOTAL | 2340.00 |

Method of Preparation

1. Pass items 1–22 through 30 mesh screen and mix them in a V-Blender or a Double Cone blender for 20 minutes.
2. Add item # 23 and mix for an additional 5 minutes.
3. Compress into tablets on a tablet press with a target weight of 2320 mg/tablet.
4. Coat the tablets with a Pharmaceutical Glaze in a coating pan until the tablet weight reaches an average of 2340 mg/tablet.

Example 10

Folic Acid Tablets

| ITEM # | INGREDIENT | MG/TABLET |
|---|---|---|
| 1 | Folic Acid 10% Trituration | 8.00 |
| 2 | Purified Shilajit/Fulvic Acid Composition | 0.80–8.00 |
| 3 | Croscarmellose Sodium | 7.50 |
| 4 | Microcrystalline Cellulose | q.s. |
| 5 | Silicon Dioxide | 2.00 |
| 6 | Stearic Acid | 5.00 |
| 7 | Pharmaceutical Glaze | q.s. |
| | TOTAL | 220.00 |

Method of Preparation

1. Pass items 1–5 through 30 mesh screen and mix them in a V-Blender or a Double Cone Blender for 20 minutes.
2. Pass item # 6 through a 30 mesh screen, add to the blend in Step 1, and mix for an additional 5 minutes.
3. Compress into tablets on a tablet press with a target weight of 220 mg/tablet.
4. Coat the tablets with a Pharmaceutical Glaze in a coating pan.

Example 11

Coenzyme Q-10 Tablets

| ITEM # | INGREDIENT | MG/TABLET |
|---|---|---|
| 1 | Coenzyme Q-10 | 50.00 |
| 2 | Purified Shilajit/Fulvic Acid Composition | 50.00–500.00 |
| 3 | Croscarmellose Sodium | 7.50 |
| 4 | Microcrystalline Cellulose | q.s. |
| 5 | Silicon Dioxide | 2.00 |
| 6 | Stearic Acid | 5.00 |
| 7 | Pharmaceutical Glaze | q.s. |
|  | TOTAL | 600.00 |

Method of Preparation
1. Pass items 1–5 through 30 mesh screen and mix them in a V-Blender or a Double Cone Blender for 20 minutes.
2. Pass item # 6 through a 30 mesh screen, add to the blend in Step 1, and mix for an additional 5 minutes.
3. Compress into tablets on a tablet press with a target weight of 600 mg/tablet.
4. Coat the tablets with a Pharmaceutical Glaze in a coating pan.

Example 12

Antioxidant Tablets

| ITEM # | INGREDIENT | MG/TABLET |
|---|---|---|
| 1 | Beta Carotine 20% 334 iu/mg | 31.25 |
| 2 | Ascorbic Acid 97% | 500.00 |
| 3 | Vitamin E Succinate 1210 Iu/g | 175.00 |
| 4 | Selenomethionine 0.5% | 20.00 |
| 5 | Zinc Monomethionine, 20% | 75.00 |
| 6 | Purified Shilajit/Fulvic Acid Composition | 20.00–200.00 |
| 7 | Microcrystalline Cellulose | q.s. |
| 8 | Croscarmellose Sodium | 10.00 |
| 9 | Silicon Dioxide | 10.00 |
| 10 | Stearic Acid | 20.00 |
| 11 | Pharmaceutical Glaze | q.s. |
|  | TOTAL | 1300.00 |

Method of Preparation
1. Pass items 1–9 through 30 mesh screen and mix them in a V-Blender or a Double Cone Blender for 20 minutes.
2. Pass item # 10 and mix for an additional 5 minutes.
3. Compress into tablets on a tablet press with a target weight of 1300 mg/tablet.
5. Coat the tablets with a Pharmaceutical Glaze in a coating pan.

Example 13

Glibenclamide Tablets

| ITEM # | INGREDIENT | MG/TABLET |
|---|---|---|
| 1 | Glibenclamide | 1.00 |
| 2 | Purified Shilajit/Fulvic Acid Composition | 10.00 |
| 3 | Lactose | 50.00 |
| 4 | Microcrystalline Cellulose | 50.00 |
| 5 | Croscarmellose Sodium | 2.00 |
| 6 | Magnesium Stearate | 1.00 |
|  | TOTAL | 114.00 |

Method of Preparation
1. Mix items 1–5 in a V-Blender or a Double Cone Blender for 15 minutes.
2. Add item # 6 and mix for an additional 5 minutes.
3. Compress into tablets on a tablet press with a target weight of 114 mg/tablet.

Example 14

Insulin Tablets

| ITEM # | INGREDIENT | MG/TABLET |
|---|---|---|
| 1 | Insulin | 30–50 IU |
| 2 | Purified Shilajit/Fulvic Acid Composition | 100–500 |
| 3 | Lactose | 50.00 |
| 4 | Microcrystalline Cellulose | q.s. |
| 5 | Croscarmellose Sodium | 2.00 |
| 6 | Magnesium Stearate | 1.00 |
|  | TOTAL | 650.00 |

Method of Preparation
1. Mix items 1–5 in a V-Blender or a Double Cone Blender for 15 minutes.
2. Add item # 6 and mix for an additional 5 minutes.
3. Compress into tablets on a tablet press with a target weight of 650 mg/tablet.

Example 15

Pentazocin Tablets

| ITEM # | INGREDIENT | MG/TABLET |
|---|---|---|
| 1 | Pentazocin | 5.00 |
| 2 | Purified Shilajit/Fulvic Acid Composition | 50.00 |
| 3 | Lactose | 50.00 |
| 4 | Microcrystalline Cellulose | 50.00 |
| 5 | Croscarmellose Sodium | 2.00 |
| 6 | Magnesium Stearate | 1.00 |
|  | TOTAL | 168.00 |

Method of Preparation
1. Mix items 1–5 in a V-Blender or a Double Cone Blender for 15 minutes.
2. Add item # 6 and mix for an additional 5 minutes.
3. Compress into tablets on a tablet press with a target weight of 168 mg/tablet.

Example 16

Folic Acid Syrup

| ITEM # | INGREDIENT | MG/5 gm |
|---|---|---|
| 1 | Folic Acid | 1.00 |
| 2 | Purified Shilajit/Fulvic Acid Composition | 10.00 |
| 3 | Citric Acid Anhydrous | 25.00 |
| 4 | Saccharin Sodium | 7.50 |
| 5 | Glycerin | 500.00 |
| 6 | Sorbitol | 3500.00 |
| 7 | Propylene Glycol | 750.00 |
| 8 | Color | q.s. |
| 9 | Sodium Benzoate | 10.00 |
| 10 | Flavor | q.s. |
| 11 | Purified Water | q.s. |
| | TOTAL | 5.00 gm |

Method of Preparation
1. Mix all the ingredients in a high shear mixer for 15 minutes.

Example 17

Coenzyme Q-10 Suspension

| ITEM # | INGREDIENT | MG/5 gm |
|---|---|---|
| 1 | Coenzyme Q-10 | 25.00 |
| 2 | Purified Shilajit/Fulvic Acid Composition | 125.00 |
| 3 | Xantham Gum | 7.5 |
| 4 | Microcrystalline Cellulose RC 591 | 40.00 |
| 5 | Purified Water | q.s. |
| 6 | Colors | q.s. |
| 7 | Flavors | q.s. |
| | TOTAL | 5.00 gm |

Method of Preparation
1. Hydrate items 3 and 4 in item 5 for 4 hours.
2. Mix the hydrated mass in Step 1 using a high shear mixer for 10 minutes.
3. Add items 1, 2, 6 and 7 and continue mixing for an additional 10 minutes.
4. De-aerate the product

Example 18

Methotrexate Tablets

| ITEM # | INGREDIENT | MG/TABLET |
|---|---|---|
| 1 | Methotrexate | 1.25 |
| 2 | Purified Shilajit/Fulvic Acid Composition | 12.5 |
| 3 | Lactose | 50.00 |
| 4 | Microcrystalline Cellulose | 53.25 |
| 5 | Croscarmellose Sodium | 2.00 |
| 6 | Magnesium Stearate | 1.00 |
| | TOTAL | 120.00 |

NOTE: Usual dose of Methotrexate is 2.5 mg/tablet. However, a lower dose is used in the example below to show that a lower dose may be equally effective when used in conjunction with purified Shilajit/Fulvic Acid composition, thus reducing the toxicity.

Method of Preparation
1. Mix items 1–5 in a V-Blender or a Double Cone Blender for 15 minutes.
2. Add item # 6 and mix for an additional 5 minutes.
3. Compress into tablets on a tablet press with a target weight of 120 mg/tablet.

Example 19

Mamoxiphen Citrate Tables

| ITEM # | INGREDIENT | MG/TABLET |
|---|---|---|
| 1 | Tamoxiphen Citrate | 10.00 |
| 2 | Purified Shilajit/Fulvic Acid Composition | 100.00 |
| 3 | Lactose | 50.00 |
| 4 | Microcrystalline Cellulose | 50.00 |
| 5 | Croscarmellose Sodium | 2.00 |
| 6 | Magnesium Stearate | 1.00 |
| | TOTAL | 213.00 |

NOTE: Usual dosages are 10 mg and 20 mg/tablet. Lower dose is used in this example.

Method of Preparation
1. Mix items 1–5 in a V-Blender or a Double Cone Blender for 15 minutes.
2. Add item # 6 and mix for an additional 5 minutes.
3. Compress into tablets on a tablet press with a target weight of 213 mg/tablet.

While the invention has been described with particular reference to certain embodiments thereof, it will be understood that changes and modifications may be made which are within the skill of the art.

Accordingly, it is intended to be bound only by the following claims, in which:

1. A stable, water-soluble delivery system for an active ingredient, which is a purified Shilajit composition obtained by extraction of crude Shilajit, containing a carrier which is purified fulvic acid characterized by a sponge-like structure punctured by voids of about 200–1000 Å in diameter and a number average molecular weight, $\overline{M}n$, of about 700–2500 which is substantially devoid of bioactive components originally present therein; and an effective amount of an active ingredient added to and filling the voids of said purified carrier.

2. A delivery system according to claim 1 wherein said purified fulvic acid carrier is at least 40% by weight of the composition and is further characterized by having a repeat unit of 3,5-dioxygenated dibenzo-α-pyrone with the general structure of:

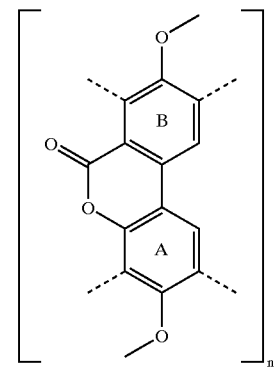

3. A delivery system according to claim 1 wherein said purified fulvic acid carrier is further characterized by having an $E_4/E_6$ absorption ratio at λ 465/665 nm of about 6–10.

4. A delivery system according to claim 1 wherein the active ingredient is selected from the group consisting of a drug, nutrient, cosmetic, cosmecutical, diagnostic agent, or a salt, isomer, or derivative of the foregoing, and mixtures thereof.

5. A delivery system according to claim 1 wherein said active ingredient is present in an amount of about 0.5 to 40% by weight of the carrier.

6. A delivery system according to claim 1 wherein the active ingredient is substantially water-insoluble.

7. A delivery system of claim 6 wherein the active ingredient is selected from the group consisting of analgesics, anti-inflammatory agents, anthelminatics, anti-arrhythmic agents, anti-bacterial agents, anti-viral agents, anti-coagulants, anti-depressants, anti-diabetics, anti-epileptics, anti-fungal agents, anti-gout gents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, beta-blockers, cardiac inotropic agents, corticosteroids, diuretics, anti-Parkinson agents, anticancer drugs, gastro-intestinal agents, histamine receptor antagonists, keratolytics, lipid regulating agents, anti-anginal agents, cox-2-inhibitors, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, sunscreens, antioxidants, anti-ageing compounds and mixtures thereof.

8. A delivery system of claim 1 further including a pharmaceutical, cosmetic or nutritionally-acceptable excipient.

* * * * *